United States Patent [19]
Brouwer et al.

[11] Patent Number: 5,486,521
[45] Date of Patent: Jan. 23, 1996

[54] PYRIMIDINYL ARYL KETONE OXIMES

[75] Inventors: Walter G. Brouwer, Guelph, Canada; Alan W. Dalrymple, Lindale, Tex.; Ethel E. Felauer, Puslinch, Canada; Paul T. McDonald, Middlebury, Conn.

[73] Assignees: Uniroyal Chemical Company, Inc., Middlebury, Conn.; Uniroyal Chemical Ltd., Elmira, Canada; Ltee, New Jersey, Canada

[21] Appl. No.: 216,207

[22] Filed: Mar. 21, 1994

[51] Int. Cl.$^6$ ............... C07D 239/54; C07D 239/56; A61K 31/505
[52] U.S. Cl. ............... 514/274; 544/312; 544/229; 504/243; 504/193; 514/63
[58] Field of Search ............... 504/243, 193; 514/274, 63; 544/312, 229

[56] References Cited

U.S. PATENT DOCUMENTS

| | | | |
|---|---|---|---|
| 4,280,999 | 7/1981 | Steelman et al. | 424/251 |
| 4,746,352 | 5/1988 | Wenger et al. | 544/312 |
| 4,760,163 | 7/1988 | Wenger et al. | 544/312 |
| 5,053,070 | 10/1991 | Gohbara et al. | 544/301 |
| 5,084,084 | 1/1992 | Satow et al. | 43/48 |
| 5,127,935 | 7/1992 | Satow et al. | 43/48 |
| 5,134,144 | 7/1992 | Brouwer et al. | 544/314 |
| 5,134,145 | 7/1992 | Brouwer et al. | 544/314 |
| 5,154,755 | 10/1992 | Satow et al. | 239/55 |
| 5,336,663 | 8/1994 | Wenger et al. | 43/48 |

FOREIGN PATENT DOCUMENTS

| | | | |
|---|---|---|---|
| 2119036 | 9/1992 | Canada | 239/54 |
| 2083071 | 12/1992 | Canada | 239/54 |
| 408382 | 7/1990 | European Pat. Off. | 413/4 |
| 542685 | 11/1992 | European Pat. Off. | 239/54 |
| 545206 | 11/1992 | European Pat. Off. | 239/54 |
| 4131038 | 9/1991 | Germany | 239/54 |

OTHER PUBLICATIONS

Wenger et al., Chemical Abstracts, vol. 119, entry 160313h (1993).
Klintz et al., Chemical Abstracts, vol. 119, entry 117271f (1993).
McCutcheon's vol. 1: Emulsifiers & Detergents (North American Edition), pp. 275–297, published 1993 by McCutcheon Division.
McCutcheon's vol. 1: Emulsifiers & Detergents (International Edition), pp. 247–268 & 271, published 1993 by McCutcheon Division.
Journal of Medicinal Chemistry, "Potential Antisecretory Antidiarrheals. 1. $\alpha_2$-Adrenergic Aromatic Aminoguanidine Hydrazones," vol. 31, No. 1, pp. 138–144, published 1988. Pifzele et al.
Tetrahedron Report No. 192, "Thionation Reactions of Lawesson's Reagents", Tetrahedron, vol. 41, No. 22, pp. 5061–5087, 1985, Great Britain. Cava et al.
Journal of Economic Entomology, "A Method of Computing the Effectiveness of an Insecticide" by W. S. Abbott, vol. 18, pp. 265–267, Apr. 1925.

*Primary Examiner*—John M. Ford
*Attorney, Agent, or Firm*—Jerome D. Drabiak

[57] ABSTRACT

The present invention is directed to a novel class of pyrimidinyl aryl ketone oximes having excellent herbicidal and insecticidal activity.

The novel compounds are represented by the structures I, Ia and Ib shown immediately below.

Herbicidal activity is particularly directed against "weed-like" grasses and broadleaf weeds while the insecticidal properties are particularly active against rice planthoppers and aphids.

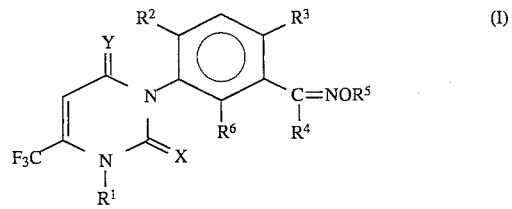

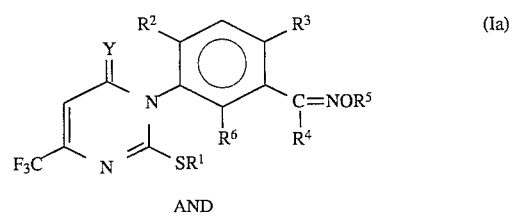

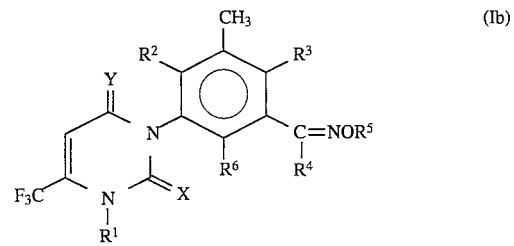

9 Claims, No Drawings

PYRIMIDINYL ARYL KETONE OXIMES

TECHNICAL FIELD

Our present invention is directed to a class of aryl pyrimidines that are useful both as herbicides and pesticides.

As herbicides, our novel compounds are particularly active against various species of grasses and broadleaf weeds, in both pre-emergent and post-emergent applications. As pesticides, our novel compounds have been found to be particularly active against aphids and rice planthoppers.

BACKGROUND ART

Undesirable, uncultivated plants—often characterized simply as "weeds"—are able to reduce yields of cultivated plants and other useful agricultural crops by competing with cultivated plants. As a result, weeds interfere with the growth of seeds, vegetables, fruits, and foliage.

Weeds are able to cause this sort of undesirable result because of the tendency of weeds to compete aggressively with cultivated plants for available light and space, moisture, and nutrients in the soil.

Furthermore, and as is well-known to those skilled in the crop-protection art, various commercially-important food plants as well as plants that are used for structural and ornamental purposes are yet additionally vulnerable to the devastation caused by insect pests.

Such sorts of pests represent a particularly serious economic threat, especially to such important cereals as rice and corn.

For this reason, there is an ongoing need for the development of crop-protection compositions that are ever more effective both against weeds and such pests as insects, mites, nematodes, and so forth.

There is, moreover, a particularly wide-spread desire throughout the industry for the development of crop-protection compositions that are not only environmentally-friendly but also satisfactorily effective at relatively low concentrations. It would thus be highly desirable for such compounds to advantageously possess activity to control weeds and other pests without causing attendant environmental difficulties.

U.S. Pat. Nos. 4,746,352 and 4,760,163—both to Wenger et al.—disclose uracil esters and their salts, which are reported to possess herbicidal properties.

In U.S. Pat. No. 4,280,999 to Steelman et al., moreover, an "insecticidal" method that utilizes uracils is discussed.

Disclosed and detailedly reported in U.S. Pat. No. 5,134,144 to Walter Brouwer, Ethel Felauer, Paul McDonald et al. (three of the present inventors) are certain uracils—ether uracils and thioether uracils—that were surprisingly discovered to possess miticidal, insecticidal, and nematocidal activities at relatively low concentrations.

Separately, in U.S. Pat. No. 5,134,145 to Brouwer, Felauer and McDonald (three of us) there are disclosed and detailedly reported certain other uracils—ester uracils—which we surprisingly discovered similarly possess miticidal, insecticidal, and nematocidal activities, also at relatively low concentrations.

OBJECTS OF INVENTION

While various prior-art compounds possessing herbicidal and/or pesticidal activity are known by those who practice their art in the field of crop-protection, there is nevertheless an ongoing need in the field of crop protection to identify and utilize ever more effective compounds, to better control weeds and other pests for the benefit of mankind.

Our present invention is directed to novel compounds of oxygen-alkylated oximes of either aromatic aldehydes or ketones.

Our novel oximes are both structurally-distinguishable and otherwise functionally-distinguishable from the prior-art compounds mentioned above.

In particular, our present novel compounds possess both herbicidal and pesticidal activity.

Various additional aspects, features and advantages of our present invention will become clear to those skilled in the crop-protection art upon reference to our detailed description, which follows.

SUMMARY DISCLOSURE OF INVENTION

A novel class of pyrimidinyl aryl ketone oximes having excellent herbicidal and insecticidal activity is disclosed.

The herbicidal activity is especially effective when directed against grasses and broadleaf weeds, while the pesticidal activity is especially effective when directed against rice planthoppers and aphids.

Also disclosed are methods for making the active compounds of our present invention.

The active compounds of our present invention may be represented by the structures I, Ia and Ib, presented below:

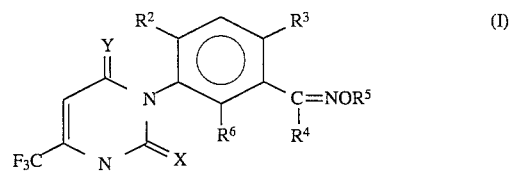

(I)

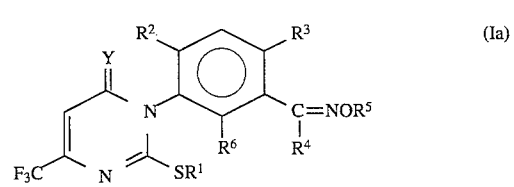

(Ia)

AND

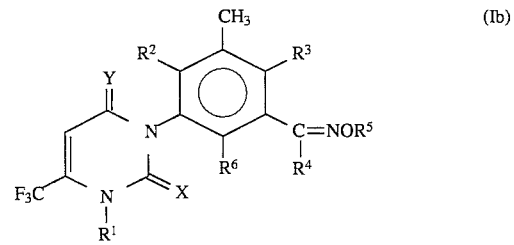

(Ib)

wherein:

$R^1$ is either hydrogen; $C_1$–$C_6$ hydrocarbyl; hydroxymethyl; alkaline earth metal; or organic base salt;

$R^2$ and $R^6$ are independently either hydrogen; halogen; or $C_1$–$C_4$ hydrocarbyl;

$R^3$ is either hydrogen; halogen; cyano; nitro; $C_1$–$C_6$ straight chain alkoxy, branched chain alkoxy or cyclic alkoxy; $C_3$–$C_6$ straight chain alkenyloxy, branched chain alkenyloxy or cyclic alkenyloxy; $C_1$–$C_6$ straight chain alkylthio or branched chain alkylthio; or $C_1$–$C_6$ hydrocarbyl;

$R^4$ is either hydrogen or $C_1$–$C_4$ hydrocarbyl;

$R^5$ is either 2-tetrahydrofuranylmethyl or $C_1$–$C_6$ hydrocarbyl; and wherein $R^5$ may be substituted either with $C_1$–$C_4$ linear alkoxy or branched alkoxy, or with trimethylsilyl, or with $C_1$–$C_6$ hydrocarbyl substituted with up to eleven (11) halogen atoms; or wherein $R^5$ may be the group Re—$CO_2$—$R^7$ wherein Re can be a $C_1$–$C_3$ alkylidene moiety and either may be substituted with $C_1$–$C_6$ linear alkyl groups or branched alkyl groups, or with from one (1) to six (6) halogen atoms; and wherein $R^7$ either is $C_1$–$C_6$ hydrocarbyl, or is the aromatic structural group shown immediately below

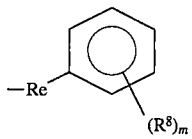

wherein Re is as defined above; and wherein $(R^8)_m$ is defined as follows:

m is an integer between 0 and 5, and $R^8$ may be independently selected from halogen; nitro; cyano; carboxy; $C_1$–$C_4$ alkoxy; $C_1$–$C_3$ alkoxycarbonyl; or $C_1$–$C_4$ hydrocarbyl; or the group $ReCOR^9$; wherein Re is as defined above; wherein $R^9$ is $C_1$–$C_4$ hydrocarbyl; phenyl substituted with $C_1$–$C_4$ hydrocarbyl; phenyl substituted with $C_1$–$C_4$ linear alkoxy or branched alkoxy; phenyl substituted with $C_1$–$C_4$ alkyl; phenyl substituted with halogen; or is the aromatic structural group shown immediately below

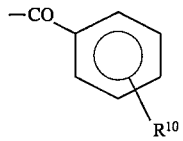

wherein $R^{10}$ is $C_1$–$C_4$ linear alkoxy or branched alkoxy; $C_1$–$C_4$ hydrocarbyl; or halogen; and wherein X and Y are independently sulfur or oxygen.

DETAILED DESCRIPTION OF INVENTION

Our present invention is directed to novel herbicidally-active, insecticidally-active, miticidally-active, and nematocidally-active compounds of the structures I, Ia and Ib, presented below:

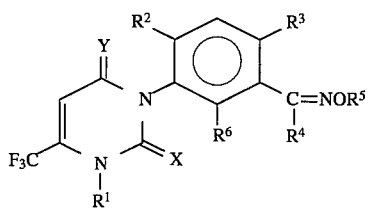

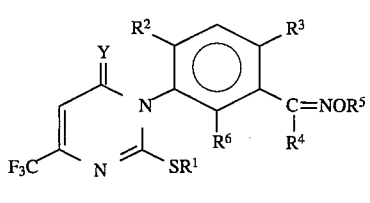

AND

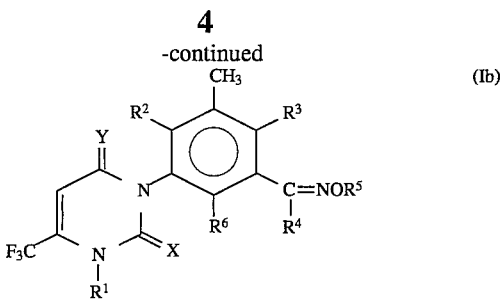

wherein:

$R^1$ is either hydrogen; $C_1$–$C_6$ hydrocarbyl; hydroxymethyl; alkaline earth metal; or organic base salt;

$R^2$ and $R^6$ are independently either hydrogen; halogen; or $C_1$–$C_4$ hydrocarbyl;

$R^3$ is either hydrogen; halogen; cyano; nitro; $C_1$–$C_6$ straight chain alkoxy, branched chain alkoxy or cyclic alkoxy; $C_3$–$C_6$ straight chain alkenyloxy, branched chain alkenyloxy or cyclic alkenyloxy; $C_1$–$C_6$ straight chain alkylthio or branched chain alkylthio; or $C_1$–$C_6$ hydrocarbyl;

$R^4$ is either hydrogen or $C_1$–$C_4$ hydrocarbyl;

$R^5$ is either 2-tetrahydrofuranylmethyl or $C_1$–$C_6$ hydrocarbyl; and wherein $R^5$ may be substituted either with $C_1$–$C_4$ linear alkoxy or branched alkoxy, or with trimethylsilyl, or with $C_1$–$C_6$ hydrocarbyl substituted with up to eleven (11) halogen atoms; or wherein $R^5$ may be the group Re—$CO_2$—$R^7$ wherein Re can be a $C_1$–$C_3$ alkylidene moiety and either may be substituted with $C_1$–$C_6$ linear alkyl groups or branched alkyl groups, or with from one (1) to six (6) halogen atoms; and wherein $R^7$ either is $C_1$–$C_6$ hydrocarbyl, or is the aromatic structural group shown immediately below

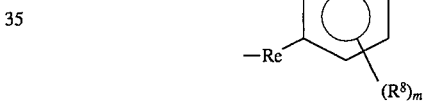

wherein Re is as defined above; and wherein $(R^8)_m$ is defined as follows:

m is an integer between 0 and 5, and $R^8$ may be independently selected from halogen; nitro; cyano; carboxy; $C_1$–$C_4$ alkoxy; $C_1$–$C_3$ alkoxycarbonyl; or $C_1$–$C_4$ hydrocarbyl; or the group $ReCOR^9$; wherein Re is as defined above; wherein $R^9$ is $C_1$–$C_4$ hydrocarbyl; phenyl substituted with $C_1$–$C_4$ hydrocarbyl; phenyl substituted with $C_1$–$C_4$ linear alkoxy or branched alkoxy; phenyl substituted with $C_1$–$C_4$ alkyl; phenyl substituted with halogen; or is the aromatic structural group shown immediately below

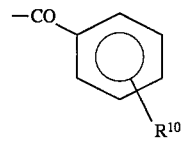

wherein $R^{10}$ is $C_1$–$C_4$ linear alkoxy or branched alkoxy; $C_1$–$C_4$ hydrocarbyl; or halogen; and wherein X and Y are independently sulfur or oxygen.

Terms & Preferred Embodiments

By "hydrocarbyl" is meant a linear, branched or cyclic, saturated or unsaturated moiety containing only hydrogen and carbon atoms.

In a general sense, we have found that the biologically-active compounds of our present invention typically have the structures I, Ia or Ib above where: $R^1$ is either hydrogen or $C_1$–$C_3$ alkyl; $R^2$ is hydrogen; $R^3$ is either hydrogen, halogen, or $C_1$–$C_3$ alkyl; $R^4$ is hydrogen; $R^5$ is $C_1$ to $C_4$ alkyl; $R^6$ is hydrogen; and X and Y are both oxygen.

While in yet other cases, we have found that the biologically-active compounds of our present invention may have the structures I, Ia or Ib above where: $R^1$ is methyl; $R^2$ is hydrogen; $R^3$ is chlorine or methyl; $R^4$ is hydrogen; $R^5$ is methyl, ethyl, tert-butyl or isopropyl; $R^6$ is hydrogen; and X and Y are both oxygen.

More particularly, we have found our novel biologically-active compound to be a particularly effective herbicide when $R^1$ is hydrogen, methyl or ethyl; when $R^2$ is hydrogen or methyl; when $R^3$ is hydrogen, chlorine or methyl; when $R^4$ is hydrogen or methyl; when $R^5$ is as listed in Table 1 below; when $R^6$ is hydrogen or methyl; when X is either O or S; and when Y is either O or S. Similarly, we have found our biologically-active compound to be a particularly effective pesticide when the above-recited chemical structural criteria are met.

Pesticidal Compositions

In yet broader respects, our present invention is directed to novel herbicidal compositions, insecticidal compositions, miticidal compositions and nematocidal compositions (hereinafter collectively referred to simply as "pesticidal compositions"). Such a pesticidal composition comprises:

(A) a pesticidally effective amount of a compound having the structures I, Ia or Ib, as presented and defined above; and (B) a suitable carrier therefor.

Industrial Applicability

Yet another aspect of our present invention is directed to a process or method for controlling undesirable populations of weeds, insects, mites and nematodes, utilizing the compound having the structures I, Ia or Ib, as presented and defined above.

Such a method comprises applying to a pre-selected site or "locus" a pesticidally-effective amount of a composition comprising:

(A) a pesticidally effective amount of a compound having the structures I, Ia or Ib, as presented and defined above; and (B) a suitable carrier therefor.

Synthesis Methods

Still another aspect of our present invention is directed to a process or method for preparing compounds having the structures I, Ia and Ib, as presented above, wherein $R^1$ through $R^6$ as well as X and Y are as defined above.

In particular, that class of compounds which is represented by structure II presented below can readily be made by synthesis procedures or methods well-known in the literature. Indeed, such methods are similar to the synthesis procedures taught in our U.S. Pat. Nos. 5,134,144 and 5,134,145, both of which were briefly mentioned above.

How To Make

Starting materials are beta-keto esters (structure II below) which furnish the enamines (structure III below) by reaction with ammonia gas. Their sodium salts (structure IV below) are made by adding the enamines (structure III shown below) to a suspension of sodium hydride in a suitable solvent such as tetrahydrofuran or dimethylformamide.

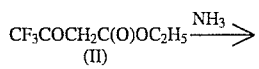
(II)

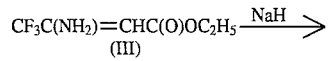
(III)

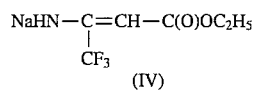
(IV)

Isocyanates and isothiocyanates (structure VI below) are made separately by reacting a suitable aromatic amine (structure V below) with phosgene or thiophosgene in a suitable solvent such as methylene chloride, ethyl acetate, toluene, xylene, or any aprotic solvent, as is known in the art.

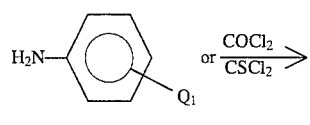
(V)

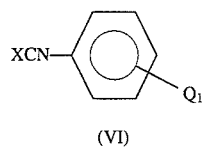
(VI)

In structures V and VI (above) the moiety $Q_1$ is utilized to illustrate the substitution position on the aromatic ring of structures depicted.

The compounds of our present invention can readily be made when a suitable sodium salt of an enamine (structure IV) is reacted with an isocyanate or isothiocyanate (structure VI) at a relatively low temperature, typically between "minus" fifty degrees Celsius (–50° C.) and "minus" seventy degrees Celsius (–70° C.) in a suitable inert solvent such as tetrahydrofuran or dimethylformamide and the reaction allowed to come to ambient temperature (ca. 25° C.) over several hours.

The resulting pyrimidine (structure I' below), wherein $R^1$ in this case only is sodium (Na) and Y is oxygen, can subsequently readily be isolated by first removing the solvent, next dissolving the residual mixture in water, and thereafter acidifying the thus-dissolved residue with a suitable mineral acid such as hydrochloric acid, sulphuric acid, phosphoric acid, or nitric acid, thereby producing the I structure in which $R^1$ is hydrogen.

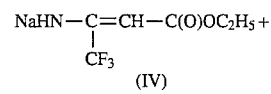
(IV)

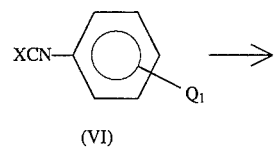
(VI)

-continued

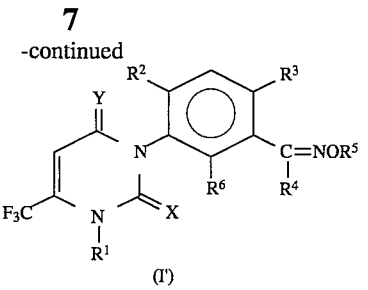

Organic base salts can readily be made by treating the compounds of structure I, Ia and Ib (wherein $R^1$ is hydrogen) with an organic base of the formula R' R'' R''' N, wherein:

the R', R'' and R''' groups are hydrogen or a hydrocarbyl group or a hydroxyalkyl group or combinations of these having from three (3) to forty-eight (48) atoms;

or two (2) or three (3) of the R', R'' and R''' groups together form a basic nitrogen-containing heterocyclic moiety (e.g. pyridine, morpholine, piperidine, etc.);

and the remaining group or groups—if any—are hydrogen; wherein such treatment takes place utilizing a suitable solvent, e.g., alcohol, tetrahydrofuran, etc.

In general, it is necessary that the organic base have sufficient strength to form a salt. That is, it is necessary that the pKa of the base be greater than about 4.85.

Subsequent removal of the solvent leaves behind the organic base salt of the compounds of our present invention, one such organic base salt being represented by structure I'' (depicted below), wherein that position which is otherwise occupied by the $R^1$ moiety of structure I (for the presently-discussed case only) is an orbital containing a free electron which provides the attached nitrogen atom with an electronegative charge, and wherein Y is oxygen:

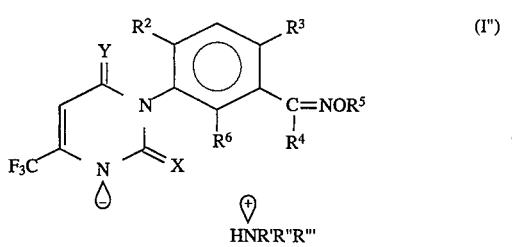

In those examples of our present invention wherein the moiety $R^1$ is alkyl, such compounds can easily be made using techniques well-known throughout the literature.

For example, when starting with compounds of structure I' wherein $R^1$ is hydrogen, treating with alkyl iodides or sulfates in the presence of a suitable base—e.g. potassium carbonate, pyridine, triethylamine—in a suitable solvent will give N-alkylated products.

An exception are those compounds wherein X is sulfur. Utilizing such an alkylation step, S-alkylated compounds of structure Ia are made.

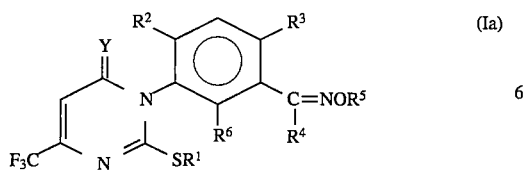

wherein $R^1$ through $R^6$ and Y have been previously described.

As stated above, the composition of our present pesticidal invention includes, as one component thereof, a carrier suitable for admixture with the active ingredient of our present: namely, a compound having the structural formula I, Ia or Ib.

The identity and type of carrier that would be suitable for purposes of the present invention may be selected from the following.

In certain applications, a suitable carrier might take the form of a finely-divided particulate solid, or granules, or pellets; or might take the form of a wettable powder, a flowable liquid, a soluble powder; while in yet other applications the carrier might take the form of an aqueous or organic solvent, an aqueous or organic dispersant, or an aqueous or organic emulsifying agent.

Among those materials which may be utilized to produce a suitable solid carrier (e.g. a carrier taking the form of pellets, granules, wettable powders, soluble powders, other finely-divided particles, and so forth) are such well-known commercially-available materials as attapulgite clay, sand, vermiculite, corn cobs, activated carbon, and mineral silicates. Among the mineral silicates are mica, talc, pyrophyllite, and the like.

In the case where the carrier is a solid, a biologically-active solid composition can readily be prepared utilizing the active ingredient of the present invention. For example, the active ingredient can be impregnated onto the solid carrier, as those skilled in the art can well appreciate.

Alternatively, the active ingredient of the present invention may be formulated into a wettable powder by grinding a suitable compound form of the active ingredient into a fine powder, and thereafter mixing or otherwise combining the resulting powder with a suitable solid carrier into which a suitable surface-active dispersing agent has been added.

The resulting wettable powder may then be dispersed in water, and thereafter sprayed onto soil surfaces, crops to be protected, and/or weeds.

In the case where the carrier is a liquid, a biologically-active liquid composition can readily be prepared utilizing the active ingredient of the present invention. In particular, a liquid solution is representative of a preferred embodiment of such a liquid composition.

In the case of a liquid solution, the active compound may readily be is dissolved in a suitable aqueous or organic solvent, as can readily be appreciated by those skilled in the art.

Among the preferred solvents employed in this invention are aromatic or aliphatic hydrocarbons. Of the hydrocarbons, toluene is particularly preferred.

Within the contemplation of our present invention, however, liquid emulsions are more commonly employed than are liquid solutions.

In particular, an emulsion is preferred because those compounds having the structural formula I or Ia are so-called "organic" compounds.

Accordingly, biologically-active formulations which include the active ingredient of our present invention would—most likely—utilize one of the most plentiful and cost-effective carriers known to man: water.

For these and other reasons water is a preferred carrier.

To produce a water-based biologically-active formulation (which includes the active ingredient of our present invention) a suitable form of the active ingredient of our present invention may advantageously be dissolved in a suitable organic solvent into which a suitable surface-active dispersing agent has been added. Water is thereafter typically added to (or otherwise combined with) the resulting mixture, to form an aqueous emulsion. The resulting aqueous emulsion may thereafter advantageously be applied to a particular location (i.e. "locus") to be protected, one such particularly preferred method of application being spraying.

Alternatively, the emulsion may utilize an organic liquid, such as oil, as the dispersant.

The surface-active dispersing agent may be any of those known to those skilled in the art.

For purposes of our present invention, examples of suitable surface-active agents are listed on pages 275–297 of *McCutcheon's* 1993 *Emulsifiers & Detergents* (Volume 1) North American Edition and on pages 247–268 and 271 of *McCutcheon's* 1993 *Emulsifiers & Detergents* (Volume 1) International Edition, both of which are published by M. C. Publishing Co. (McCutcheon Division) of Glen Rock, N.J.

With respect to still another aspect of our present invention, a method for controlling weeds and other undesirable vegetation as well as insect pests (including mites and nematodes) shall now be discussed.

In particular, such a method preferably comprises applying an effective amount of the biologically-active ingredient having the structural formula I, Ia or Ib to a pre-selected location (i.e. "locus") which is to be protected. For our novel biologically-active ingredient, the moieties $R^1$, $R^2$, $R^3$, $R^4$, $R^5$ and $R^6$ are as described above. As was also mentioned above, our biologically-active ingredient may advantageously be combined with a suitable carrier, for purposes of producing a particular formulation which, in turn, is applied to a particular locus.

In many applications which utilize the biologically-active ingredient of our invention, the concentration or weight-percentage of active ingredient in a pesticidally-effective formulation may range from between about 1% to about 95% by weight of active ingredient in the formulation, based on total weight.

In one preferred embodiment of our present invention wherein our novel biologically-active ingredient is combined with a suitable carrier and thereafter formulated into an herbicidal emulsion, the concentration or weight percent of the active ingredient in the emulsion is between about 0.002% and about 80% by weight, based on total weight of formulation.

In particular, such use involves applying about 0.01 kg (0.022 lbs) to about 10 kg (22 lbs) of our novel biologically-active ingredient per acre (i.e. about 0.022 kg to about 25 kg per hectare), when the compound of structures I, Ia or Ib is employed as a pre-emergence herbicide.

Application of the pre-emergence herbicide is typically made to the soil which contains not only weeds but also the desired crop seed. Such application is made either to the surface of the soil or 2.5 centimeters to 7.5 centimeters (1 to 3 inches) beneath the surface of the soil.

In cases where it is desirable to utilize our novel biologically-active ingredient after weed emergence ("post-emergence herbicide"), the amount of biologically-active ingredient (having the structural formula I, Ia or Ib) which is used similarly ranges between 0.01 kilograms (0.022 lbs) to 10 kgs (22 lbs) per acre (about 0.022 to about 25 kg per hectare).

Post-emergent application may occur by ground or aerial spraying of the undesired vegetation.

Those skilled in the art can well appreciate, however, that the weight percent or concentration of novel biologically-active ingredient in any particular formulation will depend upon a variety of factors including but not limited to soil type, soil pH, soil organic matter content, the quantity and intensity of rainfall before and after treatment, air and soil temperature, light intensity and light duration per day. All of these factors have an influence upon the efficacy of the biologically-active compounds of this invention when utilized as an a herbicide.

Those skilled in the art can, however, by routine experimentation, readily determine the optimum conditions for employment of our novel biologically-active compounds within the contemplation of this invention.

The following examples are now presented merely to illustrate the scope of our present invention. In this regard, the following examples are by no means intended to limit such scope.

EXAMPLE 1

Benzaldehyde, 3-[3,6-dihydro-2,6-dioxo-4-(trifluoromethyl)- 1(2H)-pyrimidinyl]-, O-1-methylethyl oxime (Compound Number 5)

Example 1 (Compound Number 5) was prepared utilizing the following steps.

Step 1: 3-Nitrobenzaldehyde (30.2 grams, 0.2 moles), potassium carbonate (25 g) and O-1-methylethyl hydroxylamine hydrochloride (25 g) in dimethoxyethane (400 mL) were combined in a reaction vessel and thereafter stirred and refluxed for 5 hours, cooled, and left overnight.

After removal of part of the solvent, water was added and the product extracted into methylene chloride. The solution was washed twice: first with saturated sodium bisulfite, next with water; and subsequently dried and evaporated, producing 27 grams of a brown oil determined as being 3-nitrobenzaldehyde O-1-methylethyl oxime.

Step 2: The above crude product in ethanol (200 mL) was reduced utilizing a Parr hydrogenator employing a catalyst of 5 % Pt on C (0.8 g). After removing the catalyst, the solvent was removed and the residual oil purified by silica gel chromatography, eluting with methylene chloride.

The resulting 20 grams (0.11 moles) of product (an oil) was determined to be 3-aminobenzaldehyde O-1-methylethyl oxime.

Step 3: The above amine in dry ethyl acetate (150 mL) was next saturated with hydrogen chloride gas until precipitation of hydrochloride salt ceased.

Utilizing stirring and heating, phosgene gas was next introduced. Within 10 minutes, the reaction was homogeneous. Phosgene passage was continued for a further 30 minutes before removing the solvent.

Upon removal of the solvent, 24 grams of an oil remained. The oil was found to be 3-Isocyanatobenzaldehyde O-1-methylethyl oxime.

Step 4: Sodium hydride (4.4 grams, 60%, 0.11 moles) was washed with petroleum ether before covering with dry THF (200 mL). With stirring and ice cooling, ethyl 3-amino-4,4,4-trifluoro-2-butenoate (20 grams) in tetrahydrofuran (50 mL) was added dropwise over 1 hour and stirred for a further 30 minutes before cooling to −70° C. The above isocyanate (of Step 3) in 25 milliliters of THF was added rapidly.

The reaction mixture was maintained at −70 ° C. for 2 hours before allowing to come to ambient temperature (ca. 25° C.) and left overnight.

The solvent was removed and water (100 mL) added, washed three times with methylene chloride and acidified. The precipitate was extracted into methylene chloride, washed with water, dried and evaporated.

Crude material was recrystallized from toluene/cyclohexane solvent to provide (13 grams of) benzaldehyde, 3-[3,6-dihydro-2,6-dioxo-4-(trifluoromethyl)- 1(2H)-pyrimidinyl]-, O-1-methylethyl oxime, found to have a melting point ("m.p.") of 181°–183° C.

Additional analytical data includes the following: C, 52.59; H, 4.05; N, 12.34. $C_{14}H_{14}F_3N_3O_3$ requires C, 52.57; H, 4.11; N, 12.32.

EXAMPLE 2

Benzaldehyde, 5-[3,6-dihydro-2,6-dioxo-4-(trifluoromethyl)- 1(2H)-pyrimidinyl]-2-methyl-, O-methyl oxime (Compound No. 20)

Example 2 (Compound Number 20) was prepared utilizing the following steps.

Step 1: 2-Methyl-5-nitrobenzaldehyde was made according to procedures set forth in *Journal of Medicinal Chemistry*, Vol. 31, No. 1, pages 138–144, published 1988.

The aldehyde thus produced (20 grams, 0. 12 moles) was refluxed, utilizing hydroxylamine hydrochloride (10 g) and triethylamine (20 mL) in ethanol (1 00 mL), over a period of 2 hours.

Upon cooling, most of the solvent was removed and poured into water. Crude oxime precipitated out, was collected on a filter, was washed with water, and was subsequently dried, yielding 14 g of a tan-colored solid having a melting point of 133°–136° C. and found to be 2-methyl-5-nitrobenzaldehyde oxime.

Step 2: The oxime (14 g, 0.1 moles) was stirred with excess methyl iodide (5 mL) and potassium carbonate (11 g) in 60 milliliters of N,N-dimethylacetamide for a period of 60 hours.

The reaction was thereafter poured into water. A cream-colored solid which separated out was collected on a filter, was washed with water, and thereafter was dried.

Recrystallization from ethanol subsequently yielded a cream-colored solid having a melting point of 100°–103° C. The cream-colored solid was found to be 2-methyl-5-nitrobenzaldehyde, O-methyl oxime.

Steps 3 and 4: Reduction and subsequent conversion of the oxime to the isocyanato analog were performed according to procedures set forth in steps 2 and 3, respectively, of Example 1, except that the hydrochloride of the benzenamine was isolated and dried before conversion to the isocyanato analog.

Step 5: In a manner similar to to procedures set forth in step 4 of Example 1, a white solid (7.8 g) having a melting point of 191°–192 ° C. was isolated and found to be: benzaldehyde, 5-[3,6-dihydro-2,6-dioxo-4-(trifluoromethyl)- 1(2H)-pyrimidinyl]-2-methyl-, O-methyl oxime.

EXAMPLE 3

Benzaldehyde, 3-[3,6-dihydro-6-oxo-2-thioxo-4-(trifluoromethyl)- 1(2H)-pyrimidinyl]-, O-methyl oxime (Compound Number 18)

Example 3 (Compound Number 18) was prepared utilizing the following steps.

Step 1: 3-Nitrobenzaldehyde, 0-methyl oxime (15 g, 0.83 mol) was reduced on the Parr hydrogenator, in accordance to procedures set forth above in step 2 of Example 1.

The crude product (10.6 grams, 0.78 moles) in methylene chloride (50 milliliters) was next treated with ice (85 grams), and stirred while a solution of thiophosgene (6.5 milliliters) in methylene chloride (15 mL) was added dropwise.

After stirring overnight, the resulting organic components were separated, washed with water, and subsequently dried and evaporated to yield 16 grams of a yellow oil found to be 3-isothiocyanatobenzaldehyde O-methyl oxime.

Step 2: As was done utilizing procedures set forth in step 4 of Example 1, the isothiocyanato derivative was converted to 10 grams of a yellow-colored solid having a melting point of 195°–197° C. and found to be the following uracil: benzaldehyde, 3-[3,6-dihydro-6-oxo-2-thioxo-4-(trifluoromethyl)- 1(2H)-pyrimidinyl]-, O-methyl oxime.

Additional analytical data includes the following: C, 47.72; H, 3.01; N, 12.67. $C_{13}H_{10}F_3N_2S$ requires C, 47.42; H, 3.04; N, 12.77.

EXAMPLE 4

Benzaldehyde, 3-[3,6-dihydro-2,6-dithioxo-4-(trifluoromethyl)- 1(2H)-pyrimidinyl]-, O-methyl oxime (Compound Number 24)

Example 4 (Compound Number 24) was prepared as follows.

The product from Example 3 (3 grams, 9.1 millimoles) in toluene (30 milliliters) together with *Lawesson's reagent (3 grams) was refluxed for 4.5 hours the first day, and the next day for an additional 5 hours.

After removing the precipitated solid, the filtrate was evaporated, and the residue subsequently recrystallized from a minimum of toluene.

The resulting product, a red-colored solid, was found to have a melting point of 196°–198° C.

Additional analytical data includes the following: C, 45.57; H, 2.90; N, 11.83. $C_{13}H_{10}F_3N_3OS_2$ requires C, 45.20; H, 2.91; N, 12.16.

* Procedures to make and use Lawesson's reagent(s) are set forth in *Tetrahedron Report Number* 192, Vol. 41, No. 22, pages 5061–5087, published 1985, and printed in Great Britain.

EXAMPLE 5

Benzaldehyde,3-[3,6-dihydro-2-oxo-6-thioxo-4-(trifluoromethyl)- 1(2H)-pyrimidinyl]-, O-2-propenyl oxime (Compound Number 22)

Example 5 (Compound Number 22) was prepared as follows.

3-[ 3,6-Dihydro-2,6-dioxo-4-(trifluoromethyl)- 1 ( 2H)-pyrimidinyl] benzaldehyde O-2-propenyl oxime (7.8 grams, 24 millimoles) was combined with Lawessons reagent (8 grams) in toluene (100 mL) and thereafter refluxed for 10 hours.

Removal of the solvent yielded a red-colored gum which was subsequently purified via silica gel chromatography, eluting with 40:60 ethyl acetate:hexane, based on weight.

A red oil was obtained which yielded 6 grams of product from toluene/cyclohexane solvent.

A repeat column eluting with methylene chloride yielded relatively purer product.

Recrystallization from toluene/cyclohexane solvent yielded 3.1 grams of a red-colored solid having a melting point of 169°–171° C.

EXAMPLE 6

Benzaldehyde, 2-chloro-5-[3,6-dihydro-2,6-dioxo- 3-methyl-4-(trifluoromethyl)- 1 (2 H)-pyrimidinyl]-, O-1-methylethyl oxime (Compound Number 4)

Example 6 (Compound Number 4) was prepared utilizing the following steps.

Step 1: 2-chloro-5-nitrobenzaldehyde (18 grams, 0.1 moles) in dimethoxyethane (100 milliliters) was combined, stirred and refluxed with O-1 -methylethylhydroxylamine hydrochloride ( 11.1 grams, 0.1 moles) and potassium carbonate (13.4 grams) for a period of 2.5 hours.

After pouring into water, the precipitated solid was extracted into methylene chloride, was washed twice with saturated sodium bisulfite, was subsequently washed with water, dried and evaporated to leave a solid (20 g) of 2-chloro-5-nitrobenzaldehyde O-1-methylethyl oxime.

Step 2: The above oxime ether (12 grams, 0.05 moles) in ethanol (200 milliters) was reduced on the Parr hydrogenator, utilizing 5 wt-% Pt on C (0.7grams) catalyst.

After filtering the resulting solution, the solvent was removed and the residual oil chromatographed on a short column of silica gel, eluting with methylene chloride.

Following removal of the eluant, 10 grams of a pale yellow-colored oil, analyzed as being 5-amino-2-chlorobenzaldehyde O-1-methylethyl oxime, remained.

Step 3: The amine (of Step 2, above) in dry ethyl acetate (100 milliliters) was subsequently saturated with hydrogen chloride gas. The hydrochloride salt of the benzenamine remained in solution.

With refluxing, this solution was treated with phosgene gas for a period of 1.5 hours.

After filtering, the reaction mixture was aspirated and subsequently the solvent removed, yielding a brown-colored oil (9.5 grams) which was used directly in the next step.

Step 4: Sodium hydride (2 grams, 0.05 moles) previously washed with petroleum ether was suspended in THF (100 milliliters) and cooled in ice. While stirring, a solution of ethyl 3-amino-4,4,4-trifluoro-2-butenoate (7.4 grams, 0.04 moles) in THF (25 mL) was added dropwise and allowed to remain for a period of 1 hour in the ice bath.

The reaction mixture was subsequently chilled to −70° C. in an acetone/dry ice bath, whereupon the isocyanato derivative (step 3 above) in THF (25 mL) was added.

The bath temperature was maintained at −70° C. for an additional period of 2 hours before removal from the bath.

Subsequently, the reaction mixture was allowed to come to ambient temperature (ca. 25° C.), and was thereafter left out at ambient conditions overnight.

The THF solvent was removed, the residue taken up in water, washed three (3) times with methylene chloride and acidified.

An oil, which separated out, was extracted into methylene chloride, washed with water, dried and evaporated, yielding a yellow-colored solid which was subsequently washed with isopropyl alcohol to leave 3 grams of material found to have a melting point of 193°–194° C.

Evaporation of the isopropyl alcohol left a residue which was recrystallized from toluene/cyclohexane solvent to give 2.7 grams of 2-chloro-5-[3,6-dihydro-2,6-dioxo-4-(trifluoromethyl)- 1(2H)-pyrimidinyl] benzaldehyde O-1-methylethyl oxime, found to have a melting point of 191°–193° C. (a second "crop" of the solid mentioned above).

Additional analytical data includes the following: C, 47.74; H, 3.49; N, 3.49; N, 11.16.

$C_{15}H_{13}ClF_3N_3O_3$ requires C, 48.00; H, 3.47; N, 11.20.

Step 5: The uracil (of step 4 above) (3.5 grams) in methylethyl ketone (40 mL) was dissolved overnight by stirring into a mixture which included potassium carbonate (3.5 grams), tetrabutylammonium iodide (0.5 grams) and methyl iodide (5 mL).

Water was added, and the product extracted into methylene chloride. The extract was washed with water, dried and evaporated to leave a solid which was recrystallized from cyclohexane/petroleum ether.

The resulting product, 2-chloro-5-[3,6-dihydro-2,6-dioxo-3-methyl-4-(trifluoromethyl)- 1(2 H)-pyrimidinyl]benzaldehyde O-1-methylethyl oxime (3 grams), was found to have a melting point of 100°–101° C.

Additional analytical data includes the following: C, 49.51; H, 3.98; N, 10.71. $C_{16}H_{15}ClF_3N_3O_3$ requires C, 49.36; H, 3.86; N, 10.80.

EXAMPLES 7 THROUGH 24

Table I (below) lists certain structural data for the various moieties of the biologically-active compounds of our present invention which have the structures I, Ia and Ib (above).

Forty-two (42) compounds are listed below in Table I.

Presented in Table 1 is structural moiety information, which we obtained utilizing infrared ("I.R.") spectroscopic data, and/or nuclear magnetic resonance ("N.M.R.") spectroscopic data, and/or elemental (e.g. C, H and N) qualitative and/or quantitative analyses.

Examples 7 through 24 (which are presented below in Table I as Compounds Numbered 1–3, 6–17, 19, 21 and 23) were prepared by us in accordance to methods set forth above in Examples 1 through 6.

Additional compounds prepared by us (Compounds Numbered 4, 5, 18, 20, 22 and 24) are also presented in Table I below.

All of the compounds for which analytical data is presented in Table I were found to be solids at room temperature (ca. 25° C.), and Table I includes the several characteristic melting points ("m.p.") of these various compounds.

TABLE I

| Cmpd Num | $R^1$ | $R^2$ | $R^3$ | $R^4$ | $R^5$ | $R^6$ | X | Y | mp (°C.) |
|---|---|---|---|---|---|---|---|---|---|
| 1 | H | H | Cl | H | $CH(CH_3)_2$ | H | O | O | 191–193 |
| 2 | H | H | Cl | H | $CH_3$ | H | O | O | 198–200 |
| 3 | $CH_3$ | H | Cl | H | $CH_3$ | H | O | O | 141–142 |
| 4 | $CH_3$ | H | Cl | H | $CH(CH_3)_2$ | H | O | O | 100–101 |
| 5 | H | H | H | H | $CH(CH_3)_2$ | H | O | O | 181–183 |
| 6 | $CH_3$ | H | Cl | H | $C(CH_3)_3$ | H | O | O | 98–99 |
| 7 | H | H | Cl | H | $C(CH_3)_3$ | H | O | O | 168–170 |
| 8 | $CH_2CH_3$ | H | Cl | H | $CH(CH_3)_2$ | H | O | O | 120–121 |
| 9 | $CH_3$ | H | Cl | H | $CH(CH_3)_2$ | H | O | O | 124–125 |
| 10 | H | H | Cl | H | $CH_3$ | H | S | O | 167–170 |
| 11 | $CH_3$ | H | Cl | H | $CH_3$ | H | — | O | 145–146 |
| 12 | H | H | Cl | H | $CH(CH_3)_2$ | H | S | O | 183–184 |
| 13 | $CH_3$ | H | Cl | H | $CH(CH_3)_2$ | H | — | O | 97–98 |
| 14 | $CH_3$ | H | Cl | H | $CH_2CH_2CH_3$ | H | O | S | 126–127 |
| 15 | $CH_3$ | H | Cl | H | $CH_2CH_2CH_3$ | H | O | O | 89–90 |
| 16 | H | H | Cl | H | $CH_2CH_2CH_3$ | H | O | O | 225–227 |
| 17 | H | H | H | H | $CH_3$ | H | S | O | 201–202 |
| 18 | H | H | H | H | $CH_3$ | H | S | O | 195–197 |
| 19 | H | H | H | H | $CH_2CH=CH_2$ | H | O | O | 138–140 |
| 20 | H | H | $CH_3$ | H | $CH_3$ | H | O | O | 191–192 |
| 21 | H | H | H | H | $C(CH_3)_3$ | H | O | O | 175–177 |
| 22 | H | H | H | H | $CH_2CH=CH_2$ | H | O | S | 169–171 |
| 23 | H | H | H | H | $CH_2CH_3$ | H | O | O | 183–184 |

TABLE I-continued

| Cmpd Num | R¹ | R² | R³ | R⁴ | R⁵ | R⁶ | X | Y | mp (°C.) |
|---|---|---|---|---|---|---|---|---|---|
| 24 | H | H | H | H | $CH_3$ | H | S | S | 196–198 |
| 25 | H | H | H | H | $CH_2.CCH$ | H | O | O | 176–178 |
| 26 | H | H | H | H | $CH_2ClC=CH_2$ | H | O | O | 139–141 |
| 27 | H | H | H | $CH_3$ | $CH(CH_3)_2$ | H | O | O | 183–184 |
| 28 | H | H | H | H | $CH_2CO_2C_2H_5$ | H | O | O | 148–151 |
| 29 | H | H | H | H | $CH_2C_6H_5$ | H | O | O | 196–198 |
| 30 | H | H | H | H | $C_5H_9(CYCLO)$ | H | O | O | 191–193 |
| 31 | H | H | $CH_3$ | H | $CH_3$ | H | O | S | 177–178 |
| 32 | H | H | H | H | $CH_2CH_2F$ | H | O | O | 187–188 |
| 33 | H | H | H | H | $CH_2CH_2F$ | H | O | S | 167–169 |
| 34 | H | H | $CH_3$ | $CH_3$ | $CH_3$ | H | O | O | 151–153 |
| 35 | H | H | H | H | $CH_2CH_2CH_3$ | H | O | O | 153–154 |
| 36 | H | H | H | H | $T_1$ | H | O | O | 185–190 |
| 37 | H | H | H | H | $CH_2CH=CHCl$ | H | O | O | 160–162 |
| 38 | H | H | H | H | $CH_3$ | $CH_3$ | O | O | 159–160 |
| 39 | H | H | H | H | $T_2$ | H | O | O | 156–158 |
| 40 | H | $CH_3$ | H | H | $CH_3$ | H | O | O | 176–178 |
| 41 | H | H | $CH_3$ | H | $CH_3$ | H | O | O | 232–233 |
| 42 | $CH_3$ | H | H | H | $CH_3$ | H | O | O | 158–159 |

Notes for Table I:

(1) Thr structure $T_1$ is

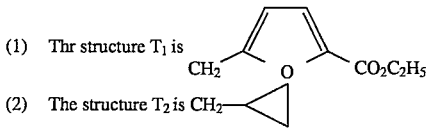

(2) The structure $T_2$ is $CH_2$—◁

(3) Compounds 1–10, 12, and 14–40 of Table I (above) are based on structure I, below.
(4) Compounds 11 and 13 are based on structure Ia, while Compounds 41–42 are based on structure Ib, below.

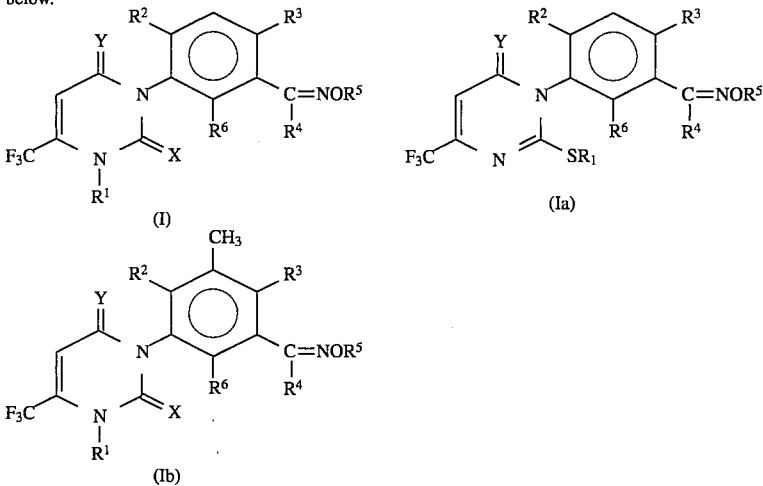

EXAMPLE 25

Preparation of Insecticidal Compositions

Each of the Compounds Numbered 1 through 42 was formed into a unique biologically-active composition. Procedures utilized to accomplish such a result can be summarized as follows.

First, for each of the forty-two (42) compounds, we dissolved 0.3 grams of each compound in ten (10) milliliters of acetone.

Each resulting solution was next diluted with ninety (90) milliliters of water with four (4) drops of ethoxylated sorbitan monolaurate, a wetting agent, added for purposes of producing a 3,000 parts-per-million ("ppm") solution.

Additional compositions—having concentrations of 1,000; 500; 200 and 100 ppm (based upon weight of biologically-active ingredient)— were prepared by serial dilution from the 3,000 ppm solution with water.

EXAMPLE 26

Rice Planthopper Foliar Test

For each of the forty-two (42) compounds, a single pot containing approximately twenty (20) Mars variety rice seedlings was treated with a unique formulation (for each of the 42 compounds) at 1,000 ppm active concentration by spraying with a spray atomizer.

One day after treatment, plants were covered with one tubular cage for each pot; and twenty (20) adult *Sogatodes oryzicola* rice delphacids were transferred into each cage.

Controls were also provided by duplicating this treatment, except that the active compounds were not applied.

Such controls included, however, the placement of twenty (20) adult rice delphacids (planthoppers) on the control rice seedling plants.

Five (5) days after transferring, counts were made of the surviving planthoppers in each pot; and percent control values were estimated in accordance with testing procedures well established in the art.

The results of the testing of rice planthoppers ("RPH") are presented below in Table II.

EXAMPLE 27

Rice Planthopper Systemic Test

Unique test formulations for nine (9) of the forty-two (42) compounds presented in Table I were prepared at 200 ppm by dissolving 0.01 grams of the compound to be tested in five (5) milliliters of acetone and adding to forty-five (45) ml of distilled water with two (2) drops of ethoxylated sorbitan monolaurate.

A 25 ml aliquot of each test solution was injected into the root zone of each pot, utilizing a hypodermic needle and syringe. Each pot held about 475 grams of moist soil.

The resulting soil concentrations of each compound to be tested was ten (10) parts per million soil concentration ("ppmsc").

When treated, each pot contained approximately twenty (20) Mars variety rice seedlings, eight (8) days old from seed.

One (1) day after treatment, the plants were covered with a tubular cage. Into each cage ten (10) adult *Sogatodes oryzicola* rice delphacids (planthoppers) were transferred.

Five (5) days after transferring, counts were made of the surviving planthoppers in each pot; and the adjusted percent control was calculated using * Abbott's formula.

*Procedures for calculating and utilizing Abbott's formula are set forth in *Journal of Economic Entomology*, Vol. 18, pages 265–267.

The results of the testing, presented as adjusted percent control of rice planthoppers ("RPH"), are listed below in Table II.

TABLE II

| Cmpd Num | RPH (Foliar) | RPH (Systemic) | SCR | GPA |
|---|---|---|---|---|
| 1 | 90 | 100 | 60 | 100 |
| 2 | 100 | 87 | 0 | 100 |
| 3 | PT | NT | 20 | NT |
| 4 | PT | NT | 20 | NT |
| 5 | 100 | 100 | 0 | 100 |
| 6 | 0 | NT | 100 | NT |
| 7 | 0 | NT | 0 | NT |
| 8 | 0 | NT | 0 | NT |
| 9 | 0 | NT | 0 | NT |
| 10 | 80 | NT | 6 | NT |
| 11 | 0 | NT | 0 | NT |
| 12 | 80 | NT | 0 | NT |
| 13 | 0 | NT | 0 | NT |
| 14 | 0 | NT | 0 | NT |
| 15 | 0 | NT | 0 | NT |
| 16 | 0 | NT | 0 | NT |
| 17 | 100 | NT | 16 | 100 |
| 18 | 0 | NT | 0 | NT |
| 19 | 100 | NT | 58 | 99 |
| 20 | 100 | 100 | 0 | 100 |
| 21 | 70 | NT | 0 | NT |
| 22 | 100 | NT | 0 | 40 |
| 23 | 100 | 100 | 0 | 100 |
| 24 | 70 | NT | 0 | NT |
| 25 | 100 | 100 | 0 | 100 |
| 26 | PT | NT | 11 | NT |
| 27 | 0 | NT | 0 | NT |
| 28 | 0 | NT | 0 | NT |
| 29 | 0 | NT | 0 | NT |
| 30 | 0 | NT | 11 | NT |
| 31 | 100 | 100 | 0 | 99 |
| 32 | 100 | 100 | 11 | 100 |
| 33 | 100 | 100 | 0 | 100 |
| 34 | 0 | NT | 0 | NT |
| 35 | 0 | NT | 0 | NT |
| 36 | 0 | NT | 0 | NT |
| 37 | 98 | NT | 0 | 90 |
| 38 | 0 | NT | 11 | NT |
| 39 | 0 | NT | 0 | NT |
| 40 | PT | NT | 100 | NT |
| 41 | 80 | NT | 16 | NT |
| 42 | 0 | NT | 16 | NT |

Notes for Table II:
(1) The term "PT" means that the compound tested was found to be completely phytotoxic at the rate evaluated.
(2) The term "NT" means "not tested."

EXAMPLE 28

Southern Corn Rootworm Test

The 3000 ppm biologically-active stock solution (described above in connection with Example 25) was diluted to 1 00 ppm.

For each of the forty-two (42) compounds reported in Table I, a unique 2.5 milliliter liquid sample was pipetted onto an individual disc of filter paper (Whatman No. 3), placed on the bottom of a 100 mm diameter petri dish. Two corn seedlings were soaked in the 100 ppm solution for one (1) hour and then transferred to the petri dish.

After twenty-four (24) hours, each dish was loaded with five (5) second instar *Diabrotica undecimpunctata* (Southern Corn rootworm) larvae.

After five (5) days, the number of live larvae was determined and the percent control, corrected by Abbott's formula, was calculated.

The results of the testing are presented under the "SCR" column in Table II, above.

EXAMPLE 29

Green Peach Aphid Foliar Test

The 3000 ppm biologically-active stock solution (described above in connection with Example 25) was diluted to 500 ppm, and used to treat tomato plants infested with green peach aphids, *Myzus persicae*, the test results being presented under the "GPA" column of Table II, above.

Percent control was estimated at six (6) days post treatment.

EXAMPLE 30

Pre-Emergence Herbicide Test

Separately, the forty-two (42) compounds listed in Table I were tested to determine their effectiveness as pre-emergence herbicides.

In this test, a 3000-ppm solution of each compound prepared as described in Example 25 was diluted to a concentration of 250 ppm by the addition of distilled water.

The forty-two (42) compounds were tested by drenching forty-six (46) milliliter aliquot samples of each 250 ppm solution described above, at a rate of about four and one-half (4.5) kilograms (10 pounds) per acre (11.2 kilograms/hectare), onto the surface of soil. The soil was contained within 11.25 centimeter-diameter (4¼ inch) plastic pots.

In such pots seeds of the following weeds had been planted:

velvetleaf, *Abutlion theophrasti* Medik., the results being presented in Table III (below) under the "VL" column;

jimsonweed, *Datura stramonium* L., the results being presented in Table III (below) under the "JW" column;

tall morningglory, *Ipomea purpurea* (L.) Roth, the results being presented in Table III under the "TM" column;

switchgrass, *Panicum virgatum* L., the results being presented in Table III under the "SG" column;

barnyardgrass, *Echinochloa crus-galli* (L.) Beauv., the results being presented in Table III under the "BG" column; and green foxtail, *Setaria viridis* (L.) Beauv., the results also being presented in Table III, under the "GF" column.

Determination of Control

Percent control of each of these weeds was determined two (2) weeks after treatment by comparison with untreated controls. Results of these tests, summarized in Table III, indicate good-to-excellent herbicidal efficacy exhibited by the compounds of this invention.

TABLE III

| Cmpd Num | JW | TM | VL | BG | GF | SG |
|---|---|---|---|---|---|---|
| 1 | 0 | 0 | 0 | 0 | 0 | 15 |
| 2 | 20 | 40 | 65 | 20 | 20 | 20 |
| 3 | 100 | 100 | 100 | 100 | 100 | 100 |
| 4 | 100 | 100 | 100 | 100 | 100 | 100 |
| 5 | 20 | 20 | 15 | 0 | 70 | 70 |
| 6 | 100 | 50 | 100 | 100 | 100 | 100 |
| 7 | 0 | 0 | 0 | 0 | 0 | 0 |
| 8 | 10 | 0 | 0 | 0 | 0 | 10 |
| 9 | 100 | 50 | 100 | 85 | 100 | 100 |
| 10 | 60 | 25 | 95 | 40 | 100 | 80 |
| 11 | 90 | 50 | 100 | 95 | 100 | 95 |
| 12 | 0 | 0 | 0 | 0 | 0 | 0 |
| 13 | 100 | 50 | 70 | 60 | 40 | 95 |
| 14 | 100 | 40 | 100 | 100 | 100 | 100 |
| 15 | 100 | 80 | 100 | 100 | 100 | 100 |
| 16 | 0 | 0 | 0 | 0 | 0 | 0 |
| 17 | 0 | 0 | 0 | 0 | 0 | 0 |
| 18 | 0 | 0 | 0 | 0 | 10 | 0 |
| 19 | 0 | 0 | 0 | 0 | 0 | 0 |
| 20 | 0 | 0 | 0 | 0 | 0 | 0 |
| 21 | 20 | 100 | 40 | 0 | 20 | 20 |
| 22 | 0 | 0 | 0 | 20 | 0 | 0 |
| 23 | 0 | 15 | 0 | 0 | 0 | 15 |
| 24 | 0 | 0 | 0 | 0 | 0 | 0 |
| 25 | 0 | 100 | 0 | 30 | 0 | 30 |
| 26 | 15 | 95 | 30 | 90 | 30 | 20 |
| 27 | 0 | 0 | 0 | 0 | 0 | 0 |
| 28 | 0 | 30 | 0 | 0 | 0 | 0 |
| 29 | 0 | 0 | 0 | 0 | 0 | 0 |
| 30 | 0 | 0 | 0 | 40 | 25 | 0 |
| 31 | 30 | 0 | 30 | 15 | 0 | 0 |
| 32 | 0 | 80 | 20 | 15 | 0 | 0 |
| 33 | 20 | 20 | 0 | 30 | 0 | 40 |
| 34 | 0 | 0 | 0 | 0 | 0 | 0 |
| 35 | 0 | 0 | 0 | 20 | 0 | 0 |
| 36 | 40 | 100 | 80 | 75 | 60 | 0 |
| 37 | 0 | 0 | 0 | 0 | 0 | 0 |
| 38 | 0 | 95 | 15 | 30 | 50 | 50 |
| 39 | 0 | 70 | 30 | 0 | 0 | 0 |
| 40 | 0 | 20 | 0 | 0 | 0 | 90 |
| 41 | 0 | 0 | 0 | 0 | 0 | 0 |

TABLE III-continued

| Cmpd Num | JW | TM | VL | BG | GF | SG |
|---|---|---|---|---|---|---|
| 42 | 0 | 15 | 50 | 0 | 20 | 30 |

EXAMPLE 31

Post-emergence Herbicide Test

To illustrate the effectiveness of the forty-two (42) compounds of this disclosure as post-emergence herbicides, a 3000 ppm stock solution (prepared in accordance with procedures set forth in Example 25) was applied to foliage of each of the weeds enumerated in Example 30.

This was accomplished by wetting the foliage of each of these weeds to the drip point with the above-described solutions.

Such solutions were applied to the foliage in the form of an atomized spray, employing a "DeVilbiss" (brand) sprayer.

The spraying of the weed foliage occurred six (6) days after foliage emergence.

Two (2) weeks following treatment with the compounds of this disclosure, percent weed control was determined, by comparison with untreated controls. The results are summarized in Table IV below.

TABLE IV

| Cmpd Num | JW | TM | VL | BG | GF | SG |
|---|---|---|---|---|---|---|
| 1 | 95 | 100 | 60 | 60 | 35 | 50 |
| 2 | 100 | 85 | 75 | 90 | 75 | 100 |
| 3 | 100 | 100 | 100 | 100 | 100 | 100 |
| 4 | 100 | 100 | 100 | 100 | 100 | 100 |
| 5 | 100 | 100 | 95 | 95 | 85 | 100 |
| 6 | 100 | 100 | 98 | 100 | 100 | 100 |
| 7 | 100 | 100 | 30 | 70 | 60 | 80 |
| 8 | 80 | 15 | 25 | 15 | 10 | 100 |
| 9 | 100 | 40 | 70 | 50 | 75 | 100 |
| 10 | 100 | 90 | 95 | 50 | 75 | 100 |
| 11 | 100 | 100 | 90 | 35 | 85 | 95 |
| 12 | 80 | 90 | 80 | 50 | 80 | 50 |
| 13 | 100 | 95 | 100 | 75 | 100 | 80 |
| 14 | 100 | 100 | 100 | 100 | 100 | 100 |
| 15 | 100 | 100 | 100 | 100 | 100 | 100 |
| 16 | 70 | 100 | 80 | 80 | 50 | 50 |
| 17 | 95 | 100 | 100 | 90 | 60 | 80 |
| 18 | 100 | 99 | 95 | 30 | 60 | 20 |
| 19 | 100 | 100 | 100 | 90 | 100 | 100 |
| 20 | 50 | 90 | 90 | 50 | 50 | 80 |
| 21 | 90 | 100 | 100 | 80 | 100 | 95 |
| 22 | 100 | 100 | 95 | 80 | 100 | 90 |
| 23 | 100 | 100 | 100 | 70 | 80 | 10 |
| 24 | 80 | 100 | 50 | 50 | 30 | 10 |
| 25 | — | 100 | 100 | 100 | 95 | 60 |
| 26 | — | 100 | 100 | 100 | 100 | 50 |
| 27 | — | 100 | 90 | 80 | 50 | 60 |
| 28 | — | 100 | 90 | 90 | 100 | 60 |
| 29 | — | 100 | 95 | 95 | 100 | 100 |
| 30 | — | 100 | 95 | 30 | 90 | 50 |
| 31 | — | 85 | 100 | 40 | 50 | 0 |
| 32 | — | 100 | 100 | 60 | 40 | 20 |
| 33 | — | 100 | 100 | 70 | 30 | 10 |
| 34 | — | 100 | 95 | 40 | 15 | 0 |
| 35 | — | 100 | 80 | 80 | 30 | 20 |
| 36 | — | 100 | 100 | 100 | 50 | 100 |
| 37 | — | 100 | 95 | 80 | 30 | 50 |
| 38 | — | 100 | 90 | 95 | 30 | 25 |
| 39 | 0 | 100 | 80 | 30 | 50 | 50 |
| 40 | 0 | 100 | 95 | 50 | 30 | 80 |
| 41 | 0 | 50 | 100 | 20 | 50 | 20 |

TABLE IV-continued

| Cmpd Num | JW | TM | VL | BG | GF | SG |
|---|---|---|---|---|---|---|
| 42 | 10 | 30 | 20 | 30 | 20 | 30 |

Summarizing the above data, we have found all of the compounds listed in Table I (above)—except for compounds Numbered 12, 20, 41 and 42—to be effective herbicides; and we have found compounds Numbered 1, 2, 5, 6, 17, 19, 20, 22, 23, 25, 31–33, 37 and 40 to be effective insecticides.

What has been described herein is a novel class of aryl pyrimidines that are useful both as herbicides and pesticides.

While our present invention has been detailedly described with reference to certain preferred embodiments, it is to be understood that the scope of our invention is not to be limited to these embodiments. Rather, it is our intent that the full scope of our present invention be as set forth in the accompanying claims.

We claim:

1. An insecticidally-active compound of structural formula I, Ia or Ib shown below wherein:

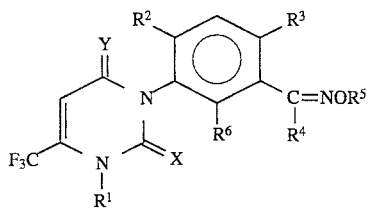

$R^1$ is hydrogen; $C_1$–$C_6$ hydrocarbyl; hydroxymethyl; alkaline earth metal; or organic base salt;

$R^2$ and $R^6$ are independently either hydrogen; halogen; or $C_1$–$C_4$ hydrocarbyl;

$R^3$ is either hydrogen; $C_1$–$C_6$ straight chain alkoxy, branched chain alkoxy or cyclic alkoxy; $C_3$–$C_6$ straight chain alkenyloxy, branched chain alkenyloxy or cyclic alkenyloxy; $C_1$–$C_6$ straight chain alkylthio or branched chain alkylthio; or $C_1$–$C_6$ hydrocarbyl; and provided that $R^3$ is not trifluoro methyl;

$R^4$ is either hydrogen or $C_1$–$C_4$ hydrocarbyl;

$R^5$ is either 2-tetrahydrofuranylmethyl or $C_1$–$C_6$ hydrocarbyl; and wherein $R^5$ may be substituted either with $C_1$–$C_4$ linear alkoxy or branched alkoxy, or with trimethylsilyl, or with $C_1$–$C_6$ hydrocarbyl substituted with up to eleven (11) halogen atoms; or wherein $R^5$ may be the group Re—$CO_2$—$R^7$ wherein Re can be a $C_1$–$C_3$ alkylidene moiety and either may be substituted with $C_1$–$C_6$ linear alkyl groups or branched alkyl groups, or with from one (1) to six (6) halogen atoms; and wherein $R^7$ either is $C_1$–$C_6$ hydrocarbyl, or is the aromatic structural group shown immediately below wherein Re is as defined above; and wherein $(R^8)_m$ is defined as follows m is an integer between 0 and 5 and $R^8$ may be independently selected from halogen; nitro; cyano; carboxy; $C_1$–$C_4$ alkoxy; $C_1$–$C_3$ alkoxycarbonyl; or $C_1$–$C_4$ hydrocarbyl; or the group ReCOR$^9$ wherein Re is as defined above; and wherein $R^9$ is $C_1$–$C_4$ hydrocarbyl; phenyl substituted with $C_1$–$C_4$ hydrocarbyl; phenyl substituted with $C_1$–$C_4$ linear alkoxy or branched alkoxy; phenyl substituted with $C_1$–$C_4$ alkyl; phenyl substituted with halogen; or is the aromatic structural group shown immediately below wherein $R^{10}$ is $C_1$–$C_4$ linear alkoxy or branched alkoxy; $C_1$–$C_4$ hydrocarbyl; or halogen; and wherein X and Y are independently sulfur or oxygen.

2. A compound of claim 1 wherein $R^1$ is hydrogen or $C_1$–$C_3$ alkyl; $R^2$ is hydrogen; $R^3$ is hydrogen, or $C_1$–$C_3$ alkyl; $R^4$ is hydrogen; $R^5$ is $C_1$ to $C_4$ alkyl; $R^6$ is hydrogen; and X and Y are both oxygen.

3. A compound of claim 1 wherein $R^1$ is methyl; $R^2$ is hydrogen; $R^3$ is methyl; $R^4$ is hydrogen; $R^5$ is methyl, ethyl, isopropyl or tert-butyl; $R^6$ is hydrogen; and X and Y are both oxygen.

4. An insecticidally-active composition effective against planthoppers and aphids, the insecticidally-active composition comprising:

A) an effective amount of the compound of claim 1; and

B) a suitable carrier therefor.

5. An insecticidally-active composition effective against planthoppers and aphids, the insecticidally-active composition comprising:

A) an effective amount of a compound of claim 2; and

B) a suitable carrier therefor.

6. An insecticidally-active composition effective against planthoppers and aphids, the insecticidally-active composition comprising:

A) an effective amount of a compound of claim 3; and

B) a suitable carrier therefor.

7. A method of controlling insects, including planthoppers and aphids, which comprises applying to a location an effective amount of the composition of claim 4, for controlling insects at the location.

8. A method of controlling insects, including planthoppers and aphids, which comprises applying to a location an effective amount of the composition of claim 5, for controlling insects at the location.

9. A method of controlling insects, including planthoppers and aphids, which comprises applying to a location an effective amount of the composition of claim 6, for controlling insects at the location.

* * * * *